(12) United States Patent
Borbély et al.

(10) Patent No.: US 9,132,098 B2
(45) Date of Patent: Sep. 15, 2015

(54) STABLE NANOCOMPOSITION COMPRISING DOXORUBICIN, PROCESS FOR THE PREPARATION THEREOF, ITS USE AND PHARMACEUTICAL COMPOSITIONS CONTAINING IT

(71) Applicants: János Borbély, Debrecen (HU); Zsuzsanna Csikós, Nyirbátor (HU); Gáborné Koncz, Göd (HU); Ildikó Schriffertne Denyicska, Debrecen (HU)

(72) Inventors: János Borbély, Debrecen (HU); Zsuzsanna Csikós, Nyirbátor (HU); Gáborné Koncz, Göd (HU); Ildikó Schriffertne Denyicska, Debrecen (HU)

(73) Assignee: BBS Nanotechnology Ltd., Debrecen (HU)

(*) Notice: Subject to any disclaimer, the term of this patent is extended or adjusted under 35 U.S.C. 154(b) by 0 days.

(21) Appl. No.: 14/134,836

(22) Filed: Dec. 19, 2013

(65) Prior Publication Data
US 2014/0294983 A1 Oct. 2, 2014

Related U.S. Application Data

(60) Provisional application No. 61/805,952, filed on Mar. 28, 2013.

(51) Int. Cl.
*A61K 9/51* (2006.01)
*A61K 31/704* (2006.01)

(52) U.S. Cl.
CPC .............. *A61K 9/5192* (2013.01); *A61K 9/5146* (2013.01); *A61K 9/5161* (2013.01); *A61K 31/704* (2013.01)

(58) Field of Classification Search
CPC . A61K 9/5146; A61K 9/5161; A61K 9/5192; A61K 31/704
USPC .......... 424/489, 490, 493, 497, 499; 977/773, 977/788
See application file for complete search history.

(56) References Cited

U.S. PATENT DOCUMENTS

| | | | |
|---|---|---|---|
| 6,645,525 B1* | 11/2003 | Woiszwillo | 424/460 |
| 7,976,825 B2* | 7/2011 | Borbely et al. | 424/9.323 |
| 8,007,768 B1 | 8/2011 | Sung et al. | |
| 2005/0058603 A1* | 3/2005 | Gao et al. | 424/9.32 |
| 2006/0073210 A1 | 4/2006 | Sung et al. | |
| 2006/0204442 A1 | 9/2006 | Tapolsky et al. | |
| 2010/0278725 A1 | 11/2010 | Liu et al. | |
| 2014/0294966 A1* | 10/2014 | Borbely et al. | 424/489 |
| 2014/0294967 A1* | 10/2014 | Borbely et al. | 424/489 |
| 2014/0296173 A1* | 10/2014 | Borbely et al. | 514/34 |

* cited by examiner

*Primary Examiner* — Jane C Oswecki
(74) *Attorney, Agent, or Firm* — Jason D. Voight (57) ABSTRACT

A nanoparticulate composition for the targeted therapeutic treatment of tumors. The stable self assembled nanocomposition according to the invention comprises (i) a carrier and targeting system comprising an optionally modified polyanion, and optionally a polycation, which may also be modified; at least one targeting agent which is linked to either the polycation/modified polycation or the polyanion/modified polyanion, or both, or to the surface of the nanoparticle; (ii) an active compound selected from the group of doxorubicin and its pharmaceutically acceptable salts, especially hydrochloride; and optionally (iii) at least one complexing agent, a metal ion, a stabilizer/formulating agent, or a PEGylating agent. The present invention furthermore relates to a process for the preparation of the above-mentioned composition, the therapeutic uses thereof, and pharmaceutical compositions containing the nanocomposition according to the invention.

16 Claims, 7 Drawing Sheets

Figure 1

Figure 2 a) HeLa measured by Real Time Analyser (Roche)

Figure 2 b) A2780 measured by Real Time Analyser (Roche)

Figure 2 c) SK-OV-3 measured by Real Time Analyser (Roche)

STABLE NANOCOMPOSITION COMPRISING DOXORUBICIN, PROCESS FOR THE PREPARATION THEREOF, ITS USE AND PHARMACEUTICAL COMPOSITIONS CONTAINING IT

This application claims priority to U.S. provisional application Ser. No. 61/805,952, filed Mar. 28, 2013, the entire disclosure of which is hereby incorporated by reference herein.

FIELD OF THE INVENTION

The present invention relates to a nanoparticulate composition for the targeted therapeutic treatment of tumours. The stable self assembled nanocomposition according to the invention comprises (i) a carrier and targeting system comprising an optionally modified polyanion, and optionally a polycation, which may also be modified; at least one targeting agent which is linked to either the polycation/modified polycation or the polyanion/modified polyanion, or both, or to the surface of the nanoparticle; (ii) an active compound selected from the group of doxorubicin and its pharmaceutically acceptable salts, especially hydrochloride; and optionally (iii) at least one complexing agent, a metal ion, a stabilizer/formulating agent or a PEGylating agent. The present invention furthermore relates to a process for the preparation of the above-mentioned composition, the therapeutic uses thereof, and pharmaceutical compositions containing the nanocomposition according to the invention.

BACKGROUND OF THE INVENTION

Doxorubicin [(7S,9S)-7-[2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione, the compound according to Formula I] is a drug used in cancer chemotherapy, often in its hydrochloride salt form.

Formula I

It is an anthracycline antibiotic, closely related to the natural product daunomycin, and like all anthracyclines, it works by intercalating DNA, with the most serious adverse effect being life-threatening heart damage. It is commonly used in the treatment of a wide range of cancers, including hematological malignancies, many types of carcinoma, and soft tissue sarcomas.

Doxorubicin interacts with DNA by intercalation and inhibition of macromolecular biosynthesis. This inhibits the progression of the enzyme topoisomerase II, which relaxes supercoils in DNA for transcription. Doxorubicin stabilizes the topoisomerase II complex after it has broken the DNA chain for replication, preventing the DNA double helix from being resealed and thereby stopping the process of replication.

The planar aromatic chromophore portion of the molecule intercalates between two base pairs of the DNA, while the six-membered daunosamine sugar sits in the minor groove and interacts with flanking base pairs immediately adjacent to the intercalation site, as evidenced by several crystal structures.

Acute adverse effects of doxorubicin can include nausea, vomiting, heart arrhythmias and Typhlitis, an acute life-threatening infection of the bowel. It can also cause neutropenia (a decrease in white blood cells), as well as complete alopecia (hair loss). A more mild side effect is discoloration of the urine, which can turn bright red for up to 48 hours after dosing. When the cumulative dose of doxorubicin reaches 550 mg/m$^2$ body surface area, the risks of developing cardiac side effects, including CHF, dilated cardiomyopathy, and death, dramatically increase. Doxorubicin cardiotoxicity is characterized by a dose-dependent decline in mitochondrial oxidative phosphorylation. Reactive oxygen species, generated by the interaction of doxorubicin with iron, can then damage the myocytes (heart cells), causing myofibrillar loss and cytoplasmic vacuolization. Additionally, some patients may develop PPE, characterized by skin eruptions on the palms of the hand or soles of the feet, swelling, pain and erythema.

DESCRIPTION OF THE STATE OF THE ART

The problem to be solved in a great number of the chemotherapeutic treatments is the non-specific effect, which means that the chemotherapeutics used is also incorporated in the sane cells and tissues, causing their death. As it can be seen above, the adverse effects of doxorubicin cause a limiting factor for the dosing regimen. There is an unmet need to find a composition comprising a carrier and targeting system, which delivers the active compound specifically to the tumour cells, thereby reducing the dose needed, and accordingly, the adverse effects on the intact tissues.

A number of attempts have been made to find a composition which satisfies the above need. U.S. Pat. No. 7,976,825 discloses a macromolecular contrast agent for magnetic resonance imaging. Biomolecules and their modified derivatives form stable complexes with paramagnetic ions thus increasing the molecular relaxivity of carriers. The synthesis of biomolecular based nanodevices for targeted delivery of MRI contrast agents is also described. Nanoparticles have been constructed by self-assembling of chitosan as polycation and poly-gamma glutamic acids as polyanion. Nanoparticles are capable of Gd-ion uptake forming a particle with suitable molecular relaxivity. There is no active agent and therapeutic use disclosed in U.S. Pat. No. 7,976,825.

U.S. Pat. No. 8,007,768 relates to a pharmaceutical composition of the nanoparticles composed of chitosan, a negatively charged substrate, a transition metal ion, and at least one bioactive agent for drug delivery. The nanoparticles are characterized with a positive surface charge configured for promoting enhanced permeability for bioactive agent delivery. The pharmaceutical composition consists of a shell portion that is dominated by positively charged chitosan and a core portion, wherein the core portion consists of the positively charged chitosan, a transition metal ion, one negatively charged substrate, at least one bioactive agent loaded within the nanoparticles, and optionally a zero-charge compound. The composition may contain at least one bioactive agent selected from the group of exendin-4, GLP-1, GLP-1 analog, insulin or insulin analog. Doxorubicin is not mentioned among the possible active agents.

WO2007019678 relates to an implantable device comprising a biocompatible and biodegradable matrix impregnated with a bioactive complex suitable for selectively targeting the lymphatic system, wherein the bioactive complex comprises one or more particle forming materials and among other bioactive agents e.g. doxorubicin. The implantable device according to the document comprises a biocompatible and biodegradable matrix impregnated with a bioactive complex suitable for selectively targeting the lymphatic system, wherein the bioactive complex comprises one or more particle forming materials and one or more bioactive agents. The particles are microparticles or nanoparticles or their combination of microparticles and nanoparticles and the particle size is from about 0.3 µm to about 11.2 µm. Unlike our invention, there is no targeting agent in the above-mentioned composition, and the specific effect is attempted to be achieved by implantation.

US2006073210 relates to a method of enhancing intestinal or blood brain paracellular transport configured for delivering at least one bioactive agent in a patient comprising administering nanoparticles composed of [gamma]-PGA and chitosan. The administration of the nanoparticles takes place orally. The chitosan is a low molecular weight chitosan (50 kDa) and dominates on a surface of said nanoparticles. The surface of said nanoparticles is characterized by a positive surface charge. The nanoparticles have a mean particle size between about 50 and 400 nanometers and are formed via a simple and mild ionic-gelation method. The nanoparticles are loaded with a therapeutically effective amount of at least one bioactive agent. In the above-mentioned prior art document doxorubicin is not mentioned as possible therapeutically active agent. Furthermore, though the composition may enhance the penetration of the blood brain carrier, targeting of the therapeutics has not been solved by the invention.

WO2005025508 relates to magnetically targetable particles comprising at least one magnetic component. The particles are capable of delivering selectively to a site or organ a biologically active substance, e.g. doxorubicin for in vivo medical diagnosis and/or treatment. The particles are prepared by e.g. encapsulation processes. Also described are methods for making the particles, methods for localized in vivo delivery of a biologically active agent utilizing the particles, a kit for the administration of the particles, as well as a method for sterilizing the particles. The composition disclosed has a different structure from that of our invention, using different components.

The state of the art failed to solve the above-mentioned problem that is the reduction of the adverse effects of doxorubicin through the decrease of the incorporated active agent by its targeted delivery. There is an unsatisfied need to provide for a stable composition for the targeted therapeutic treatment of tumours using doxorubicin. We performed systematic research in the field and, as a result of our surprising findings, completed our invention.

BRIEF DESCRIPTION OF THE SEVERAL VIEWS OF THE DRAWINGS

The figures have the meaning as follows:

FIG. 2 a-c: HeLa, A2780 and SK-OV-3 measured by Real Time Analyser (Roche). These figures show the growth profile of HeLa cells (a), A2780 cells (b) and SK-OV-3 cells (c) after treating with doxorubicin drug molecules (D), doxorubicin-loaded nanoparticles (NP), control cells (C) and pegylated NP-s (NP-PEG, FIG. 2 c). The injected volume contained the same concentration of doxorubicin.

FIG. 3 a-i: MTT results. This figure shows the MTT assay results of doxorubicin drug molecules (D) doxorubicin-loaded PGA (PD) doxorubicin-loaded nanoparticles (NP), pegylated nanoparticles (NP-PEG(2000)) and the Doxil using HeLa cell line (a), A2780 cell line (b) A549 cell line (c) MCF-7 cell line (d, f) KB, SK-OV-3 cell line (g, h) and LNCaP cell line (i).

DETAILED DESCRIPTION OF THE INVENTION

We have surprisingly found that a stable, self assembling nanocomposition may be prepared by using a polycation together with a polyanion when preparing the carrier of the pharmaceutically active agent. The nanocarrier system according to the present invention consists of at least four components: a polycation, a polyanion, an active agent, which is doxorubicin or its hydrochloride salt, and a targeting molecule, which may be linked to the polycation, the polyanion or both, or to the surface of the nanoparticle. The composition may additionally contain a complexing agent, a metal ion, a stabilizer/formulating agent, or a PEGylating agent though these are not necessarily included the composition. The formation of the nanoparticles takes place by the self assembling of the polyelectrolites.

Accordingly, in its first aspect the invention relates to a stable self assembled composition comprising (i) a carrier and targeting system comprising an optionally modified polyanion, and optionally a polycation, which may also be modified; at least one targeting agent which is linked to either the polycation/modified polycation or the polyanion/modified polyanion, or both, or to the surface of the nanoparticle;

(ii) an active compound selected from the group of doxorubicin and its pharmaceutically acceptable salts, especially hydrochloride; and optionally (iii) at least one complexing agent, metal ion and stabilizer/formulating agent, or a PEGylating agent.

In a preferred embodiment, the biopolymers are water-soluble, biocompatible, biodegradable polyelectrolyte biopolymers.

One of the polyelectrolyte biopolymers is a polycation, positively charged polymers, which is preferably chitosan or any of its derivatives. In a preferred embodiment in the composition according to the invention the polycation is chitosan, or the modified polycation. E.g. in the composition according to the invention the polycation may be chitosan, the modified polycation may be selected from the derivatives of chitosan, especially CH-EDTA, CH-DOTA, CH-DTPA, CH-FA, CH-LHRH, CH-RGD, CH-EDTA-FA, CH-FA-EDTA, CH-DOTA-FA, CH-FA-DOTA, CH-DTPA-FA, CH-FA-DTPA.

The other type of the polyelectrolyte biopolymers is a polyanion, a negatively charged biopolymer. Preferably the polyanion is poly-gamma-glutamic acid (PGA); the modified polyanion is selected from the derivatives of PGA, especially PGA-DOX, PGA-FA, PGA-FA-DOX, PGA-LHRH, PGA-RGD, PGA-CA, PGA-CA-DOX.

The derivatives of biopolymers can be their cross-linked nanosystems, biopolymer-complexone products, or other grafted derivatives resulted in modifications of biopolymers with other molecules, e.g. PEG oligomers.

Preferably the targeting agent is selected from the group of small molecules, preferably folic acid (FA), peptides, preferably LHRH, RGD, a monoclonal antibody, preferably Transtuzumab.

Preferably the complexing agent is selected from the group of diethylenetriaminepentaacetic acid (DTPA), 1,4,7,10-tetracyclododecane-N,—N',N",N'"-tetraacetic acid (DOTA), ethylene-diaminetetraacetic acid (EDTA), 1,4,7,10-tetraazacyclododecane-N,N',N"-triacetic acid (DO3A), 1,2-diaminocyclohexane-N,N,N',N'-tetraacetic acid (CHTA), ethylene glycol-bis(beta-aminoethylether) N,N,N',N',-tetraacetic acid (EGTA), 1,4,8,11-tetraazacyclotradecane-N,N',N",N'"-tetraacetic acid (TETA), and 1,4,7-triazacyclononane-N,N',N"-triacetic acid (NOTA), but is not limited to these materials.

The metal ion is selected from the group of calcium, magnesium, gallium, gadolinium and copper ion; and the stabilizer/formulating agent is selected from the group of glucose, physiological salt solution, PBS, or any combination thereof.

In a preferred embodiment, the drug molecules are ionically or covalently attached to the bioanion or its derivatives via their functional groups. In case of covalent conjugation, water-soluble carbodiimide, as coupling agent is used to make stable amide bonds between the drug molecules and the biopolymers via their carboxyl and amino functional groups in aqueous media.

As used in the present invention the abbreviations below have the following meanings:

PGA means poly-gamma-glutamic acid
PAA means polyacrylic acid
HA means hyaluronic acid
ALG means alginic acid
CH means chitosan
FA means folic acid
LHRH means luteinsing hormone releasing hormone
RGD means arginin-glycin-aspartate amino acid sequence
DOX means doxorubicin
DTPA means diethylene-triamine-pentaacetic acid
DOTA means 1,4,7,10-tetracyclododecane-N,—N',N",N'"-tetraacetic acid
EDTA means ethylene-diaminetetraacetic acid
DO3A means 1,4,7,10-tetraazacyclododecane-N,N',N"-triacetic acid
CHTA means 1,2-diaminocyclohexane-N,N,N',N'-tetraacetic acid
EGTA means ethylene glycol-bis(beta-aminoethylether) N,N,N',N',-tetraacetic acid
TETA means 1,4,8,11-tetraazacyclotradecane-N,N',N",N'"-tetraacetic acid
NOTA means 1,4,7-triazacyclononane-N,N',N"-triacetic acid
PGA-FA means poly-gamma-glutamic acid-bound folic acid
PGA-DOX means poly-gamma-glutamic acid-bound doxorubicin
PGA-FA-DOX means folic acid-PGA-bound doxorubicin
PGA-LHRH means poly-gamma-glutamic acid-bound luteinsing hormone releasing hormone
PGA-RGD means poly-gamma-glutamic acid-bound arginin-glycin-aspartate amino acid sequence
PAA-FA means polyacrylic acid-bound folic acid
PAA-LHRH means polyacrylic acid-bound luteinsing hormone releasing hormone
PAA-RGD means polyacrylic acid-bound arginin-glycin-aspartate amino acid sequence
HA-FA means hyaluronic acid-bound folic acid
HA-RGD hyaluronic acid-bound arginin-glycin-aspartate amino acid sequence
HA-LHRH hyaluronic acid-bound luteinsing hormone releasing hormone
ALG-FA means alginic acid-bound folic acid
ALG-LHRH means alginic acid-bound luteinsing hormone releasing hormone
ALG-RGD means alginic acid-bound arginin-glycin-aspartate amino acid sequence
CH-EDTA means chitosan-bound ethylene-diaminetetraacetic acid
CH-DOTA means chitosan-bound 1,4,7,10-tetracyclododecane-N,—N',N",N'"-tetraacetic acid CH-DTPA means chitosan-bound diethylene-triamine-pentaacetic acid
CH-FA means chitosan-bound folic acid
CH-LHRH means chitosan-bound luteinsing hormone releasing hormone
CH-RGD means chitosan-bound arginin-glycin-aspartate amino acid sequence
CH-EDTA-FA means chitosan-bound ethylene-diaminetetraacetic acid and folic acid
CH-FA-EDTA means chitosan-bound folic acid and ethylene-diaminetetraacetic acid
CH-DOTA-FA means chitosan-bound 1,4,7,10-tetracyclododecane-N,—N',N",N'"-tetraacetic acid and folic acid
CH-FA-DOTA means chitosan-bound folic acid and 1,4,7,10-tetracyclododecane-N,—N',N",N'"-tetraacetic acid
CH-DTPA-FA means chitosan-bound diethylene-triamine-pentaacetic acid and folic acid
CH-FA-DTPA means chitosan-bound folic acid and diethylene-triamine-pentaacetic acid
EDC*HCl means (1-ethyl-3-(3-dimethylaminopropyl)-carbodiimide methiodide)
DMSO means dimethyl-sulphoxide
NaOH means sodium-hydroxide
PA means polyanion
PC means polycation
PD means doxorubicin loaded polymer
NP means nanoparticle
HOBt means 1-hydroxybenzotriazole hydrate
TEA means tryethylamine
PEG means polyethylene glycol
MeO-PEG-NH$_2$ means methoxy polyethylene glycol amine
FA-PEG-NH$_2$ means folic acid polyethylene glycol amine
CA means citric acid
PGA-CA means poly-gamma-glutamic acid bound citric acid
PGA-CA-DOX means doxorubicin loaded PGA-CA
FA-PEG means pegylated folic acid
PGA-PEG-FA means poly-gamma-glutamic acid bound pegylated folic acid
PGA-PEG-FA-DOX means doxorubicin loaded PGA-PEG-FA
NP-PEG means pegylated nanoparticles
NP-PEG-FA means nanoparticles bound FA-PEG.

A preferred self-assembled composition according to the present invention is characterized by any one or more of the following features:

(i) the average size of the nanoparticles in swollen state is in the range between 30 to 500 nm, preferably 60 to 200 nm, more preferably about 80 to 120 nm;

(ii) the proportion of the polycation to the polyanion is about 1:20 to 20:1 based on the weight of the agents;

(iii) the polyanion has a pH of 7.5 to 10; a molecular weight of 10 000 Da to 1.5 MDa and a concentration of 0.01 to 2 mg/ml;

(iv) the polycation has a pH of 3.5 to 6; a molecular weight of 60 to 320 kDa and a concentration of 0.01 to 2 mg/ml.

In its second aspect the present invention relates to a process for the preparation of the above mentioned composition according to the invention, characterized in that it comprises the steps of (i) a targeting agent is bound covalently to the polycation and/or the polyanion;

(ii) the active agent is bound covalently or by an ionic bond to the polyanion;

(iii) the polycation and the polyanion are contacted with each other, preferably in a ratio of 1:20 to 20:1 based on the weight of the agents, thus are reacted with each other to self-assemble;

(iv) optionally the other components are added to the reaction mixture.

In a preferred embodiment the polyanion used in the process according to the invention has a pH of 7.5 to 10; a molecular weight of 10 000 Da to 1.5 MDa and a concentration of 0.01 to 2 mg/ml; and the polycation used has a pH of 3.5 to 6; a molecular weight of 60 to 320 kDa and a concentration of 0.01 to 2 mg/ml.

Prior to the reaction of the polyelectrolites any one of them or all of them is/are bound to a targeting agent by a covalent bond, thus the nanoparticles will cumulate in the tumourous cells. Furthermore, an active agent according to the present invention is bound to the polyanion, either by covalent or by ionic bond. It is critical to form such a bond between the active compound and the polyanion, which is likely to be split by the time of being incorporated in the target cell, and the active compound is released.

On reaction of the polycation and the polyanion a self-assembly takes place, contracting the molecule and resulting in a stable nanosystem. The thus formed nanoparticles possess negative surface charge and a narrow range of size distribution, which ensure the uniform physical and chemical characteristics. The resulting composition is a hydrophilic nanosystem, and forms stable colloid systems in water.

The nanosystem can be designed to achieve compositions with exactly expected features. The type of the self-assembling biopolymers, the order of admixing of the polycation and the polyanion (or their modified derivatives), the molecular weight, the mass ratio, the concentration and the pH of the the polycation and the polyanion (or their modified derivatives) will result in different features (size, surface charge, active agent content, targeting agent content, etc.) of the system. The selection of the above elements may be done by the skilled person, knowing the object without undue experimentation.

Furthermore, the present invention relates to a stable self-assembled composition comprising (i) a carrier and targeting system comprising an optionally modified polycation, and an optionally modified polyanion; at least one targeting agent which is linked to either the polycation/modified polycation or the polyanion/modified polyanion, or both, or to the surface of the nanoparticle;

(ii) an active compound selected from the group of doxorubicin; and optionally (iii) at least one complexing agent, metal ion, stabilizer/formulating agent, or a PEGylating agent, which is obtainable by the above-mentioned process according to the invention.

In its third aspect the invention relates to a pharmaceutical composition comprising the composition according to the invention together with pharmaceutically acceptable auxiliary materials, preferably selected from group of glucose, physiological salt solution, and PBS, or any combination thereof.

Furthermore, the present invention relates to the use of the composition according to the invention or the pharmaceutical composition according the invention for the preparation of a medicament; and the use of the composition or the pharmaceutical composition according to the invention for the treatment of tumours. Finally the invention relates to a method for the treatment of a subject in need for the treatment of tumours, especially human cervical adenocarcinoma (HeLa, KB), human ovary carcinoma (A2780, SK-OV-3), human lung adenocarcinoma (A549, H1975), human breast carcinoma (Jimt-1, MCF-7, MDA-MB-231), human prostate carcinoma (PC-3, LNCaP), human skin melanoma (HT168-M1/9), human colon adenocarcinoma (HT29), human melanoma (WM983A) and human metastatic melanoma (WM983B) cell line by administering to the subject an effective amount of the composition or the pharmaceutical composition according to the present invention.

The nanoparticles according to the present invention may be further modified, as follows:

1. the PEGylation of the nanoparticle: the prepared nanoparticles may be coated with PEG (poly-ethylene-glycol). The distribution of the nanoparticles thus obtained in the body does not differ from the organ-distribution of the non-PEGylated nanoparticles. With the use of the PEGylated nanoparticles the side effects, e.g. the non-desired accumulation of the nanoparticle in the organs, or the weigh-loss may be decreased;

2. the PEG-folic-acidation of the nanoparticle: the prepared nanoparticle is coated with a PEG-chain, which contains folic acid at the end of the chain, thereby better targeting can be achieved;

3. PEG-folic acid association with PGA: the folic acid content of polymers, and thereby nanoparticles can be increased by linking the folic acid to the polymers through a PEG-chain rather than directly. By this method the reaction efficiency may be increased. It is noted that in each three cases a PEG with shorter or longer chain may be of use, e.g. with 750 Da, 2000 Da, 3400 Da, 5000 Da molecular weight;

4. The modification of PGA with citric acid: the PGA-chain may be modified with citric acid, thereby the number of carboxyl moieties may be increased (there will be 3 carboxyl moiety instead of one), thus an opportunity is given to bind more folic acid or more medicine on the polymer. The reaction is illustrated by the scheme below.

Poly-γ-glutamic acid

Citric acid

Accordingly, a further aspect of the present invention is a composition according to the invention, wherein
a) the prepared nanoparticles are further coated with PEG (poly-ethylene-glycol); and/or
b) the prepared nanoparticles are further coated with a PEG-chain, which contains folic acid at the end of the chain; and/or
c) the folic acid content of polymers, and thereby nanoparticles is further increased by linking the folic acid to the polymers through a PEG-chain.

EXAMPLES

Preparation of the Formulation According to the Invention

Nanoparticles can be formed by adding polyanion(s) to polycation(s) or the other way round. The addition order of the polyelectrolytes affects the size of the nanoparticles and to a small extent also their surface charge. In both cases the nanoparticle has the structure of a statistical ball, however, significantly smaller particles with narrower size distribution are formed if the polycation (PC) is added to the polyanion (PA).

By using polyanions of a smaller molar mass, the formed nanoparticle is also smaller. The molar mass of the polycation only slightly influences the size of the nanoparticle.

With higher polymer concentration, the size of the formed nanoparticles is also bigger. This may be achieved by the preparation of the nanoparticles in dilute polymer solution, and the solution of the formed nanoparticles with narrow size distribution is then concentrated.

Tests of the Effectiveness of the Compositions According to the Invention

The internalization and accumulation of the nanosystem according to the present invention were proved on different cell lines in vitro; the cytotoxicity of the nanosystem was tested by investigating the viability of the cells using the MTT method, on among others human cervical adenocarcinoma (HeLa, KB), human ovary carcinoma (A2780, SK-OV-3), human lung adenocarcinoma (A549, H1975), human breast carcinoma (Jimt-1, MCF-7, MDA-MB-231), human prostate carcinoma (PC-3, LNCaP), human skin melanoma (HT168-M1/9), human colon adenocarcinoma (HT29), human melanoma (WM983A) and human metastatic melanoma (WM983B) cell line During the MTT tests in some nanosystems modest aggregation was experienced in the microscopic images, which means that some of the compositions in vitro were failed to retain their stability to the expected extent. It was found that the chemical stability of the particles can be improved by adding a complexing agent to one or all of the polymers, thus, aggregation can be avoided, however, in these cases larger particles are formed, and it is a concern that their internalization into the cells is decreasing. This problem may be solved by using a metal ion, especially alkali earth metals, preferably calcium, magnesium, gallium, gadolinium or copper ion, as the system in these cases undergo a contraction.

The effects of glucose, physiological saline solution, infusion base solutions and different buffers on the size, size distribution and stability of the nanoparticles were investigated. It was found that these solutions cause a decrease in the size distribution of the particles and accordingly, their stability will improve.

The xCELLigence RTCA HT Instrument from Roche Applied Science uses gold electrodes at the bottom surface of microplate wells as sensors to which an alternating current is applied. Cells that are grown as adherent monolayers on top of such electrodes influence the alternating current at the electrodes by changing the electrical resistance (impedance). The degree of this change is primarily determined by the number of cells, strength of the cell-cell interactions, interactions of the cells with the microelectrodes and by the overall morphology of the cells. The RTCA Software calculates the Cell Index (CI) as the relative change in measured impedance to represent cell status. The normalized cell index (NCI—plotted on y axis) is the relative cell impedance presented in the percentage of the value at the base-time. NCI shows rate of the surface covered by cells. NCI increases by rise of cell-number or cell-size. For example NCI value in a culture treated with a proliferation inhibitory drug first can increase (because the cell-size grows) and after decreases (because the cell-number reduces).

The MTT test is a colorimetric assay that measures the reduction of yellow 3-(4,5-dimethythiazol-2-yl)-2,5-diphenyl tetrazolium bromide (MTT) by mitochondrial succinate dehydrogenase. The MTT enters the cells and passes into the mitochondria where it is reduced to an insoluble, coloured (dark purple) formazan product. The cells are then solubilised with an organic solvent (dimethyl sulfoxide) and the released, solubilised formazan reagent is measured spectrophotometrically. Since reduction of MTT can only occur in metabolically active cells the level of activity is a measure of the viability of the cells. This method can therefore be used to measure cytotoxicity, proliferation or activation.

Cell Lines:

| Cell line | Type of carcinomacell |
|---|---|
| HeLa | Human cervicaladenocarcinomacell line |
| A2780 | Human ovarycarcinoma cell line |
| AD2780 | Human ovarycarcinoma cell line (dox. res.) |
| SK-OV-3 | Human ovary adenocarcinoma cell line |
| A549 | Human lung adenocarcinoma cell line |
| H1975 | Human lung adenocarcinoma cell line |
| JIMT-1 | Human breastcancer cell line |
| MCF-7 | Human breastcarcinoma cell line |
| PC-3 | Human prostatecarcinoma cell line |
| LNCaP | Human prostatecarcinoma cell line |
| KB | Human cervicalcarcinoma cell line |
| HT168-M1/9 | Human skinmelanoma cell line |
| MDA-MB-231 | Human breastcarcinoma cell line |
| HT29 | Human colon adenocarcinoma cell line |
| WM983A | Human melanoma cell line |
| WM983B | Human metastaticmelanoma cell line |
| HaCaT | Human keratinocyte cell line |
| HeDe | Rat tumor cell line |

EXAMPLES

Example 1

Preparation of Folated Poly-Gamma-Glutamic Acid

Poly-gamma-glutamic acid (m=50 mg) was solubilized in water (V=50 ml), then 1-(3-dimethylaminopropyl)-3-ethylcarbodiimide hydrochloride (EDC*HCl) (m=22 mg) was added to the solution. The mixture was stirred for 30 minutes while cooling on ice. Then 32 mg folic acid dissolved in 10 ml DMSO was added to the reaction mixture and stirred at room temperature in the dark for 24 hours. The folated poly-gamma-glutamic acid was purified with membrane filtration. The preparation of the covalently bound folated poly-gamma-glutamic acid is illustrated by the reaction scheme below.

The preparation of the PGA-PEG-FA is illustrated by the reaction scheme below.

Example 2

PEG-Folic Acid Association with PGA

Poly-gamma-glutamic acid (m=300 mg) was solubilized in water (V=300 ml), then HOBt (m=94 mg) was added to the PGA solution. The solution was stirred at 4° C. for 15 minutes, then 1-(3-dimethylaminopropyl)-3-ethylcarbodiimide hydrochloride (EDC*HCl) (m=445 mg in 15 ml water) was added to the solution. The mixture was stirred for 10 minutes while cooling on ice, then folic acid-PEG-amine (NH$_2$-PEG-NH-FA) ((m=100 mg in 10 ml water) and TEA (m=235 mg) was added to the reaction mixture and stirred at room temperature in the dark for 24 hours. The PGA-FA-PEG was purified with membrane filtration.

Example 3

Modification of PGA with Citric Acid

PGA solution (V=30 ml, c=0.5 mg/ml) was stirred at 4° C. for 30 minutes. 1-(3-dimethylaminopropyl)-3-ethylcarbodiimide hydrochloride (m=44 mg) and 1-hydroxybenzotriazole hydrate (HOBt) (m=31.4 mg) was dissolved in (c=1 mg/ml) NaHCO$_3$ solution, then the mixture was added to the PGA solution. The solution was stirred for 2 hours, then citric acid (CA) (m=24.4 mg in 2 ml water) was added to the reaction mixture and stirred at 4° C. for 4 hours, then at room temperature for 20 hours.

The PGA-CA was purified with membrane filtration.

Example 4

Preparation of Folated Chitosan

A solution of 1-(3-dimethylaminopropyl)-3-ethylcarbodiimide hydrochloride (EDC*HCl) and FA in anhydrous DMSO was prepared and stirred at room temperature until FA was well dissolved (1 h). Chitosan was dissolved in 0.1 M hydrochloric acid, to produce a solution with a concentration of 1 mg/ml, and then adjusted to pH 5.5 with 0.10 M sodium hydroxide solution. After the dropwise addition of EDC*HCl (m=5.1 mg in 1 ml distilled water) to the chitosan solution (V=20 ml), the reaction mixture was stirred for 10 min. Then folic acid (m=8.5 mg in dimethyl sulfoxide, V=1 ml) was added to the reaction mixture. The resulting mixture was stirred at room temperature in the dark for 24 h. It was brought to pH 9.0 by dropwise addition of diluted aqueous NaOH and was washed three times with aqueous NaOH, and once with distilled water. The polymer was isolated by lyophilization.

Example 5

Preparation of Chitosan-DTPA Conjugate

Chitosan (m=15 mg) was solubilized in water (V=15 ml); its dissolution was facilitated by dropwise addition of 0.1 M HCl solution. After the dissolution, the pH of chitosan solution was adjusted to 5.0. After the dropwise addition of DTPA aqueous solution (m=11 mg, V=2 ml, pH=3.2), the reaction mixture was stirred at room temperature for 30 min, and at 4° C. for 15 min after that, EDC*HCl (m=8 mg, V=2 ml distilled water) was added dropwise to the reaction mixture and stirred at 4° C. for 4 h, then at room temperature for 20 h. The chitosan-DTPA conjugate (CH-DTPA) was purified by dialysis.

Example 6

Preparation of Doxorubicin Loaded Poly-Gamma-Glutamic Acid—Ionically Bound

Poly-gamma-glutamic acid (m=1.5 mg) was dissolved in water (V=5 ml) and then adjusted to pH 9.5. Doxorubicin (DOX) solution (V=400 µl) with a concentration of c=2 mg/ml was added to the PGA solution and the reaction was stirred at room temperature in the dark for 24 h. The doxorubicin-loaded PGA was purified by dialysis.

Example 7

Preparation of Doxorubicin Loaded Poly-Gamma-Glutamic Acid—Covalently Bound

Poly-gamma-glutamic acid (m=5 mg) was dissolved in water (V=10 ml) and then adjusted to pH 5.5. The PGA solution (0.5 mg/ml) was cooled with ice for 20 minutes, then 0.6 ml EDC*HCl solution was added (1 mg/ml). The reaction mixture was stirred for one hour while cooling on ice and then for one our without ice. Then it was stirred again with ice for 20 minutes and 0.6 ml doxorubicin solution (2 mg/ml) was added. It was stirred for 24 hours, then purified by membrane filtering.

The preparation of the covalently bound doxorubicin loaded poly-gamma-glutamic acid is illustrated by the reaction scheme below.

Example 8

Preparation of Doxorubicin Loaded Folated-Poly-Gamma-Glutamic Acid (PGA-FA-DOX)—Covalently Bound 20 ml 0.5 mg/ml folated-PGA was stirred for 15 minutes at pH=6. 6.17 mg doxorubicin was added dropwise to the solution and the reaction was stirred for 30 minutes at room temperature, then for 15 minutes at 4° C. 3.16 mg EDC*HCl was dissolved in 1 ml DMSO and mixed 1.40 mg HOBt dissolved in 1 ml DMSO to produce a mixture. The mixture was added to the reaction and the reaction was stirred at 4° C. for 4 hours then room temperature for 20 hours. The PGA-FA-DOX was purified with membrane filtration.

Example 9

Figure 4:
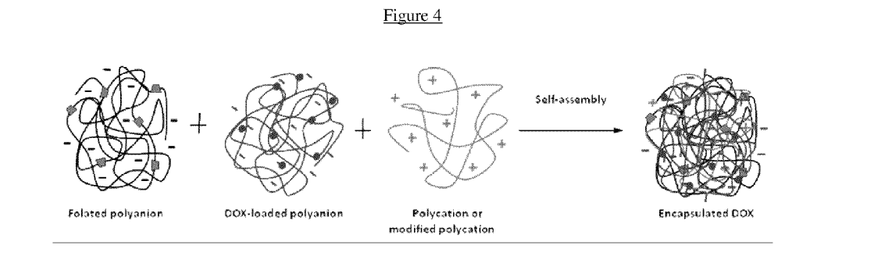
FIG. 4: The preparation of targeting, doxorubicin loaded, self-assembled nanoparticles.

Preparation of Targeting, Doxorubicin Loaded, Self-Assembled Poly-Gamma-Glutamic Acid/Chitosan Nanoparticles Folated PGA solution (c=0.5 mg/ml) and DOX-loaded PGA solution (c=0.5 mg/ml) were mixed at a ratio of 1:1. The pH of mixture was adjusted to 9.5. Chitosan was dissolved in water (c=0.5 mg/ml), and the pH was adjusted to 4.0. Chitosan solution (V=1 ml) was added to the PGA mixture (V=2 ml), and was stirred at room temperature for 15 min. The preparation of targeting, doxorubicin loaded, self-assembled nanoparticles can be seen in FIG. 4. It noted that the nanosystem can be prepared by a number of methods, the scheme is only one example for the preparation of the three phase system.

Example 10

Preparation of Targeting, Doxorubicin Loaded, Self-Assembled Poly-Gamma-Glutamic Acid/Chitosan Nanoparticles DOX-loaded PGA solution was prepared with a polymer concentration of c=0.3 mg/ml. The pH of the solution was adjusted to 9.5. Folated chitosan was dissolved in aqueous medium with a concentration of 0.3 mg/ml, and the pH was adjusted to 4.0. Folated chitosan solution (V=1 ml) was added dropwise to the DOX-loaded PGA solution (V=2 ml) under continuous stirring.

Example 11

Preparation of Targeting, Doxorubicin Loaded, Self-Assembled Poly-Gamma-Glutamic Acid/Chitosan Nanoparticles Folated PGA solution was prepared with a polymer concentration of 0.3 mg/ml. The pH of the solution was adjusted to 9.0. DOX-loaded PGA solution was prepared with a polymer concentration of c=0.3 mg/ml. The pH of the solution was adjusted to 9.5. Chitosan-EDTA was dissolved in aqueous medium with a concentration of 0.3 mg/ml, and the pH was adjusted to 4.0. Folated PGA (V=1.5 ml) was added by dripping to the DOX-loaded PGA solution (1.5 ml), then 1 ml CH-EDTA solution was added dropwise to the reaction mixture. After 5 minutes of stirring 0.4 ml calcium solution (1 mg/ml) was added by dripping.

Example 12

Preparation of Pegylated NP-s (Pegylation with MeO-PEG-NH$_2$ 2000 Da)

4.65 mg MeO-PEG-NH$_2$ was added drop wise to 15 ml doxorubicin loaded NP (c$_{polymer}$=0.3 mg/ml) and the solution was stirred for 30 minutes at room temperature, then for 15 minutes at 4° C. 1.38 mg EDC*HCl was dissolved in 1 ml distilled water and mixed 0.63 mg HOBt dissolved in 1 ml distilled water to produce a mixture. The mixture and 0.94 mg TEA was added to the reaction. The reaction was stirred at 4° C. for 4 hours then room temperature for 20 hours.

The pegylated NP was purified with membrane filtration.

Figure 6:
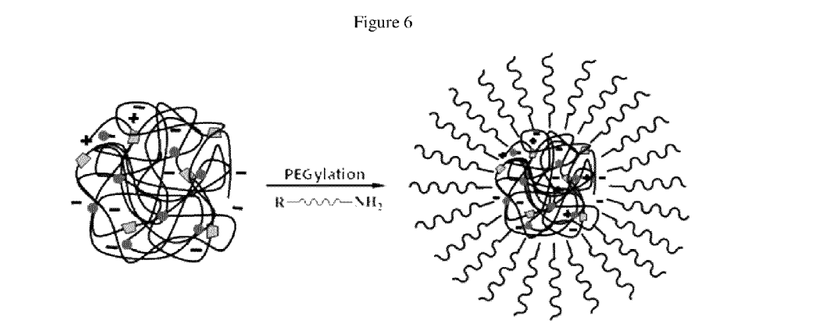
FIG. 6: The preparation of pegylated NP-s reaction scheme.

The preparation of pegylated NP-s is illustrated by the reaction scheme shown in FIG. 6.

In the R-PEG amine used in the reaction R may stand for e.g. methoxy, methyl, hydroxyl, thiol moiety, etc.

Example 13

Preparation of NP-PEG-FA (Pegylation with FA-PEG-NH$_2$ 3400 Da)

7.91 mg FA-PEG-NH$_2$ was added drop wise to 15 ml doxorubicin loaded NP (c$_{polymer}$=0.3 mg/ml) and the solution was stirred for 30 minutes at room temperature, then for 15 minutes at 4° C. 1.38 mg EDC*HCl was dissolved in 1 ml distilled water and mixed 0.63 mg HOBt dissolved in 1 ml distilled water to produce a mixture. The mixture and 0.94 mg TEA were added to the reaction. The reaction was stirred at 4° C. for 4 hours then room temperature for 20 hours.

The NP-PEG-FA was purified with membrane filtration.

Figure 7:
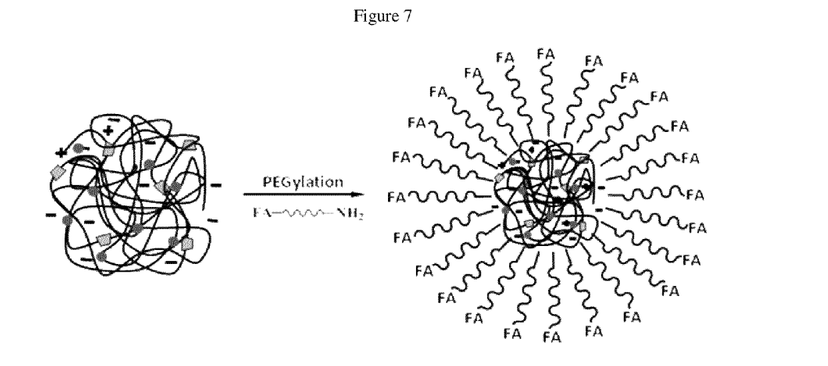
FIG. 7: The preparation of NP-PEG-FA reaction scheme.

The preparation of NP-PEG-FA is illustrated by the reaction scheme shown in FIG. 7.

The Results in Connection with the Targeting of the Nanoparticles

Figure 5A:
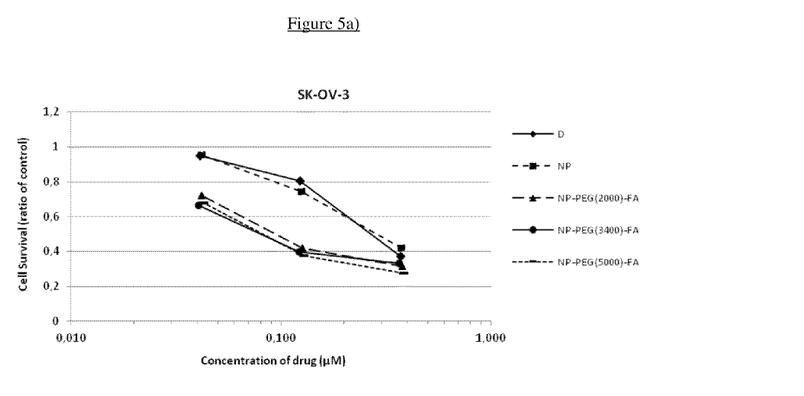
FIG. 5a-b: The effect of coating of the nanoparticles with PEG-folic acid on the internalization by the cells.
Figure 5B:
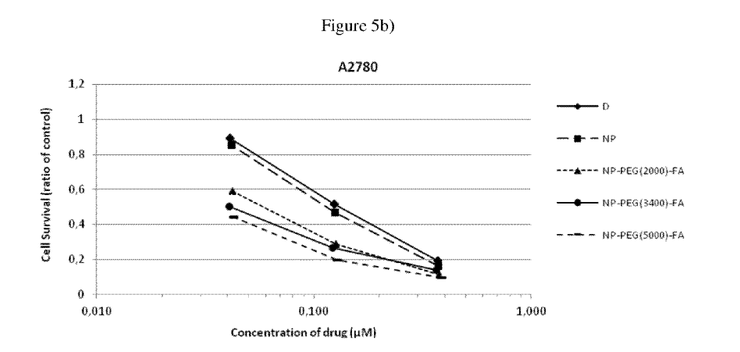

When the surface of the nanoparticles was coated with PEG-folic acid of different length, it was experienced that the nanoparticles was more effectively internalized by the cells, as compared to the normal nanoparticles and doxorubicin. The results can be seen in FIGS. 5a) to 5b).

Example 14

Characterization of Self-Assembled, Drug-Loaded Nanoparticles

The hydrodynamic size and size distribution of particles was measured using a dynamic light scattering (DLS) technique with a Zetasizer Nano ZS (Malvern Instruments Ltd., Grovewood, Worcestershire, UK). This system is equipped with a 4 mW helium/neon laser with a wavelength of 633 nm and measures the particle size with the noninvasive backscattering technology at a detection angle of 173°. Particle size measurements were performed using a particle-sizing cell in the automatic mode. The mean hydrodynamic diameter was calculated from the autocorrelation function of the intensity of light scattered from the particles. Electrokinetic mobility of the nanoparticles was measured in folded capillary cell (Malvern) with a Zetasizer Nano ZS apparatus.

Example 15

Cellular Uptake of Self-Assembled, Drug-Loaded Nanoparticles

Internalization and selectivity of nanoparticulates was investigated in cultured human cancer cells overexpressing folate receptors by using confocal microscopy and flow cytometry. The samples were imaged on an Olympus Fluo-View 1000 confocal microscope. Excitation was performed by using the 488 nm line of an Ar ion laser (detection: 500-550 nm) and the 543 nm line of a HeNe laser (detection: 560-610 nm) to image Alexa 488 and Alexa 546 respectively. Images were analyzed using Olympus FV10-ASW 1.5 software package. Flow cytometric analysis (BD FACSArray Bioanalyzer System) was carried out with a single-cell suspension, and only the live cells were gated based on forward and side scatter dot plots.

Example 16

MTT Assay of Self-Assembled, DOX-Loaded Nanoparticles

MTT assay of the DOX-loaded biopolymers and nanoparticles was performed using an UT-6100 Microplate Reader.

Approximately 10 000 HeLa cells/well were plated in 96-well plate. The cells were incubated at 37° C. for 24 h. After that the cells were treated with the drug-loaded systems, and incubated at 37° C. for another 24 h. 20 µl MTT reagent was added to each well, and the plate was incubated for 4 h at 37° C. when purple precipitate was clearly visible under microscope, 200 µl DMSO was added to all wells, including control wells. The absorbance of the wells was measured at 492 nm.

The effect of pH and addition ratios on the size, in case of 0.3 mg/ml polymer concentrations:

|    | pH of the polyanion (PA) | pH of the polycation (PC) | PA:PC ratio | Size (nm) |
|----|------|---|-----|-----|
| 1. | 7.5 | 4 | 1:1 | 106 |
| 2. | 7.5 | 4 | 2:1 | 112 |
| 3. | 7.5 | 4 | 3:1 | 129 |
| 4. | 7.5 | 5 | 1:1 | 109 |
| 5. | 7.5 | 5 | 2:1 | 122 |
| 6. | 7.5 | 5 | 3:1 | 148 |
| 7. | 8.5 | 4 | 1:1 | 106 |
| 8. | 8.5 | 4 | 2:1 | 119 |
| 9. | 8.5 | 4 | 3:1 | 136 |
| 10. | 8.5 | 5 | 1:1 | 94 |
| 11. | 8.5 | 5 | 2:1 | 119 |
| 12. | 8.5 | 5 | 3:1 | 142 |
| 13. | 9.5 | 4 | 1:1 | 104 |
| 14. | 9.5 | 4 | 2:1 | 126 |
| 15. | 9.5 | 4 | 3:1 | 126 |
| 16. | 9.5 | 5 | 1:1 | 98 |
| 17. | 9.5 | 5 | 2:1 | 122 |
| 18. | 9.5 | 5 | 3:1 | 124 |

Effect of Glucose Solution on the Size and Polydispersity of Nanoparticles Through a Specific Example:

Formulation of a nanoparticle (NP): mixing PGA-FA-DOX (pH=9.5) and CH-EDTA (pH=4) in a ratio of 2PA:1PC, polymer concentration: 0.3 mg/ml The nanoparticle is mixed with a 75% glucose solution in a ratio so that the final glucose concentration is 5%.

| | |
|---|---|
| Size of the original NP (nm) | 119 |
| Polydispersity of the original NP | 0.172 |
| Size of NP mixed with glucose solution (nm) | 111 |
| Polydispersity of NP mixed with glucose solution | 0.157 |

In Vivo Results

Tumor was induced in mice by implanting SK-OV-3 human ovary adenocarcinoma cells s.c. in upper region of back of SCID mice and allowing the tumors to develop to appreciable size over 40 days (30 mm3). The comparative efficacy study of six i.v. injection (day 43, 50, 57, 65, 71 and 78) of 5% glucose, doxorubicin (DOX) 3.8 mg/kg, NP 12.8 mg/kg and NP-PEG 3.8 mg/kg) was evaluated over 104 days. In this table there are the tumor volume of mice on 78th day after tumor inoculation (data represent mean±SEM of five mice per_group) and body weight of mice on 78th day after tumor inoculation (Data represent mean±STDEV of five mice per group). The table below discloses the comparative efficacy study in SK-OV-3 s.c. xenograft SCID mouse model of ovary cancer.

| Treatment (total dose of 6 injections) | Tumor volume (mm$^3$) | Animal weight (g) |
|---|---|---|
| 5% glucose | 661.1 ± 309 | 24.46 ± 1.50 |
| DOX (23 mg/kg) | 294.8 ± 216 | 22.54 ± 0.77 |
| NP (17 mg/kg) | 108.9 ± 30 | 23.06 ± 0.12 |
| NP-PEG (23 mg/kg) | 169.2 ± 55 | 24.94 ± 0.66 |

Figure 1:
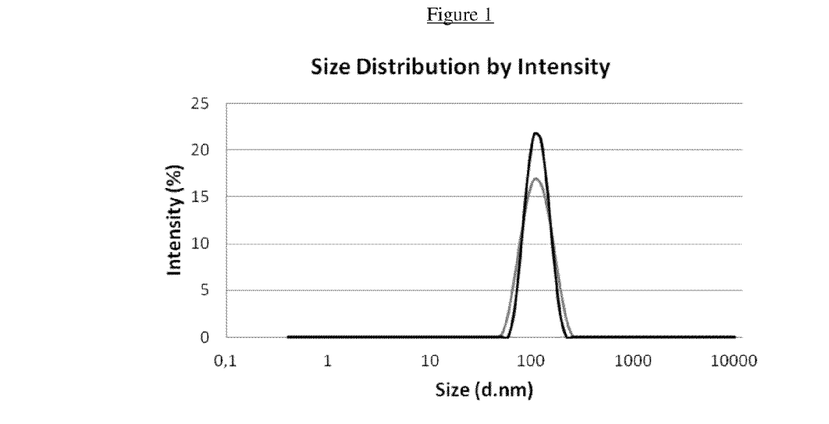
FIG. 1: Size distributions by intensity. This figure shows the size distribution of doxorubicin-loaded nanoparticles by intensity in which nanocarriers were constructed by self-assembly of biopolymers at a concentration of 0.3 mg/ml, at given ratios, where the CH-EDTA solution was added into the PGA-FA-DOX solution.
Figure 2:
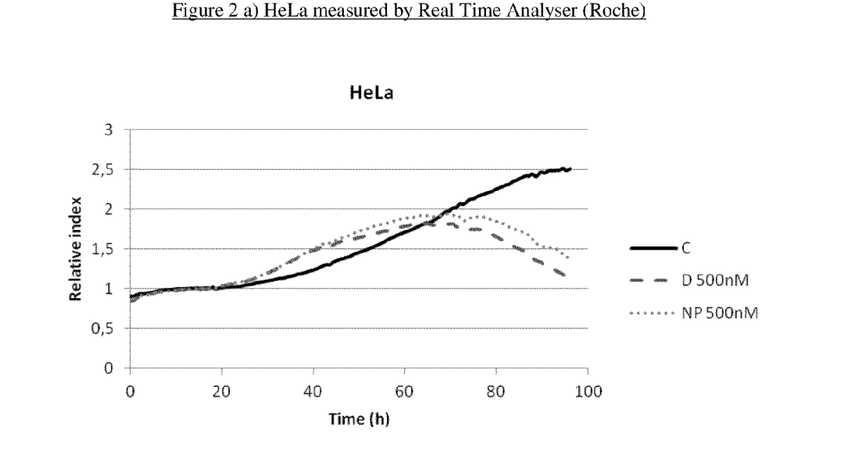
Figure 3:
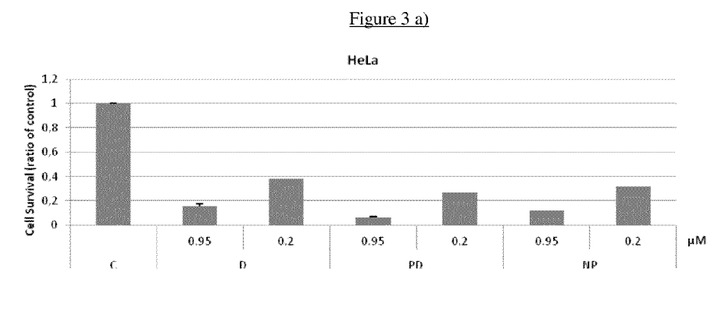

The results show (see FIGS. 1, 2) that the effect of doxorubicin and the pegylated and nonpegylated doxorubicin-loaded nanoparticles is similar on the studied tumor cell lines; however the nanoparticles due to their targeting ligand deliver the drug molecules into the tumor cells and minimize the side effect of the drug. Effect of drug was studied for several days. The results support that effect of drug is long-drawn, the living cell index did not increase either after 3 days.

Results of MTT assay (see FIG. 3) confirm that the doxorubicin was successfully conjugated and the doxorubicin-loaded nanoparticles decreased the cell viability of several tumor cells considerably. The viability of tumor cells was investigated in a function of dose of drug-loaded nanoparticles. It was established that folate-targeted doxorubicin-loaded nanoparticles considerably decrease the cell viability depending on the dose of nanoparticles as well as the amount of delivered drug molecules.

The invention claimed is:

1. A stable self-assembled composition comprising
   (i) a carrier and targeting system comprising nanoparticles formed by self-assembly of an optionally modified polyanion, and optionally a polycation, which may also be modified, said nanoparticles having a surface; at least one targeting agent which is linked to either the polycation/modified polycation or the polyanion/modified polyanion, or both, or to the surface of the nanoparticle;
   (ii) an active compound selected from the group of doxorubicin and its pharmaceutically acceptable salts covalently bound to the polycation and/or the polyanion;
   (iii) a PEGylating agent; and optionally
   (iv) at least one complexing agent, metal ion, or stabilizer/formulating agent, wherein the nanoparticles are coated with PEG, and/or PEG-chain containing targeting agent at the end of the chain.

2. The composition according to claim 1, wherein the polycation is selected from the group consisting of chitosan, and its derivatives, the modified polycation is selected from the group consisting of chitosan-EDTA, chitosan-DOTA, chitosan-DTPA, chitosan-FA, chitosan-LHRH, chitosan-RGD, CH-EDTA-FA, CH-FA-EDTA, CH-DOTA-FA, CH-FA-DOTA, CH-DTPA-FA, and CH-FA-DTPA; the polyanion is selected from the group consisting of poly-gamma-glutamic acid (PGA), polyacrylic acid (PAA), hyaluronic acid (HA), and alginic acid (ALG); the modified polyanion is selected from the group consisting of PGA-DOX, PGA-FA, PGA-FA-DOX, PGA-CA, PGA-CA-DOX, PGA-LHRH, PGA-RGD, PAA-FA, PAA-LHRH, PAA-RGD, HA-FA, HA-RGD, HA-LHRH, ALG-FA, ALG-LHRH, and ALG-RGD; the targeting agent is selected from the group consisting of folic acid (FA), LHRH, RGD, and a monoclonal antibody; the complexing agent is selected from the group consisting of diethylenetriaminepentaacetic acid (DTPA), 1,4,7,10-tetracyclododecane-N,—N',N'',N'''-tetraacetic acid (DOTA), ethylene-diaminetetraacetic acid (EDTA), 1,4,7,10-tetraazacyclododecane-N,N',N''-triacetic acid (DO3A), 1,2-diaminocyclohexane-N,N,N',N'-tetraacetic acid (CHTA), ethylene glycol-bis(beta-aminoethylether) N,N,N',N',-tetraacetic acid (EGTA), 1,4,8,11-tetraazacyclotradecane-N,N', N'',N'''-tetraacetic acid (TETA), and 1,4,7-triazacyclononane-N,N',N''-triacetic acid (NOTA); the metal ion is selected from the group consisting of calcium, magnesium, gadolinium, gallium and copper ion; and the stabilizer/formulating agent is selected from the group consisting of glucose, physiological salt solution, PBS, and any combination thereof.

3. The composition according to claim 1, which is characterized by any one or more of the following features:
   (i) an average size of the nanoparticles is in a range between 30 to 500 nm;
   (ii) the proportion of the polycation to the polyanion is about 1:20 to 20:1 based on the weight of the agents;
   (iii) the polyanion has a pH of 7.5 to 10; a molecular weight of 10 000 Da to 1.5 MDa and a concentration of 0.01 to 2 mg/ml; and
   (iv) the polycation has a pH of 3.5 to 6; a molecular weight of 60 to 320 kDa and a concentration of 0.01 to 2 mg/ml.

4. A process for the preparation of the composition according to claim 1, characterized in that it comprises the steps of
   (i) a targeting agent is bound covalently to the polycation and/or the polyanion;
   (ii) the active agent is bound covalently to the polyanion;
   (iii) the polycation and the polyanion are contacted with each other in a ratio of 1:20 to 20:1 based on the weight of the agents, thus are reacted with each other to self-assemble;
   (iv) optionally the at least one complexing agent, metal ion, or stabilizer/formulating agent are added to the reaction mixture.

5. The process according to claim 4, wherein the polyanion used has a pH of 7.5 to 10; a molecular weight of 10 000 Da to 1.5 MDa and a concentration of 0.01 to 2 mg/ml; and the polycation used has a pH of 3.5 to 6; a molecular weight of 60 to 320 kDa and a concentration of 0.01 to 2 mg/ml.

6. A stable self-assembled composition comprising
   (i) a carrier and targeting system comprising an optionally modified polyanion, and optionally a polycation, which may also be modified; at least one targeting agent which is linked to either the polycation/modified polycation or the polyanion/modified polyanion, or both;
   (ii) an active compound selected from the group of doxorubicin and its pharmaceutically acceptable salts covalently bound to the polycation and/or the polyanion; and optionally
   (iii) at least one complexing agent, metal ion or stabilizer/formulating agent,
   which is obtainable by the process according to claim 4.

7. The composition according to claim 1, wherein
   a) the prepared nanoparticles are further coated with PEG (poly-ethylene-glycol); and/or
   b) the prepared nanoparticles are further coated with a PEG-chain, which contains folic acid at the end of the chain; and/or
   c) the folic acid content of the optionally modified polycation and/or the optionally modified, and thereby nanoparticles is further increased by linking the folic acid to the optionally modified polycation and/or the optionally modified polyanion through a PEG-chain.

8. A pharmaceutical composition comprising the composition according to claim 1 together with pharmaceutically acceptable auxiliary materials.

9. A method for the treatment of a subject in need of the treatment of tumours selected from the group consisting of human cervical adenocarcinoma, human ovary carcinoma, human lung adenocarcinoma, human breast carcinoma, human prostate carcinoma, human skin melanoma, human colon adenocarcinoma, human melanoma and human metastatic melanoma cell line, by administering to the subject an effective amount of the composition according to claim 1.

10. The composition according to claim 2, wherein the monoclonal antibody is Transtuzumab.

11. The composition according to claim 3, wherein the average size of the nanoparticles is in the range between 60 to 200 nm.

12. The composition according to claim 3, wherein the average size of the nanoparticles is in the range between 80 to 120 nm.

13. The composition according to claim 1, wherein the pharmaceutically acceptable salt is hydrochloride salt.

14. The composition according to claim 6, wherein the pharmaceutically acceptable salt is hydrochloride salt.

15. The composition according to claim 8, wherein the pharmaceutically acceptable auxiliary materials are selected from the group consisting of glucose, physiological salt solution, and PBS.

16. The composition according to claim 1, wherein the nanoparticles are coated with PEG-chain containing targeting agent at the end of the chain.

* * * * *